(12) United States Patent
Granja Filho

(10) Patent No.: US 9,017,348 B2
(45) Date of Patent: Apr. 28, 2015

(54) INSUFFLABLE PROSTHESIS FOR ANASTOMOSIS

(76) Inventor: Luiz Gonzaga Granja Filho, Recife/PE (BR)

(*) Notice: Subject to any disclaimer, the term of this patent is extended or adjusted under 35 U.S.C. 154(b) by 1238 days.

(21) Appl. No.: 12/303,830

(22) PCT Filed: Jun. 6, 2007

(86) PCT No.: PCT/BR2007/000147
§ 371 (c)(1),
(2), (4) Date: Jun. 18, 2010

(87) PCT Pub. No.: WO2007/140563
PCT Pub. Date: Dec. 13, 2007

(65) Prior Publication Data
US 2010/0249812 A1    Sep. 30, 2010

(30) Foreign Application Priority Data
Jun. 6, 2006    (BR) .................................... 0602736

(51) Int. Cl.
*A61B 17/08* (2006.01)
*A61B 17/11* (2006.01)
*A61F 2/06* (2013.01)

(52) U.S. Cl.
CPC .......... *A61B 17/11* (2013.01); *A61B 2017/1107* (2013.01); *A61F 2/064* (2013.01)

(58) Field of Classification Search
USPC ................................................. 606/153, 151
See application file for complete search history.

(56) References Cited

U.S. PATENT DOCUMENTS

| | | | |
|---|---|---|---|
| 3,254,650 A | 6/1966 | Collito | |
| 3,265,069 A | 8/1966 | Healey, Jr. et al. | |
| 3,774,615 A | 11/1973 | Lim et al. | |
| 4,366,819 A | 1/1983 | Kaster | |
| 4,753,236 A | 6/1988 | Healey | |
| 6,293,968 B1 | 9/2001 | Taheri | |
| 2002/0013601 A1* | 1/2002 | Nobles et al. | ................. 606/193 |

FOREIGN PATENT DOCUMENTS

FR       2869527 A1   11/2005
WO  2002102282 A1   12/2002

* cited by examiner

*Primary Examiner* — Gregory Anderson
(74) *Attorney, Agent, or Firm* — Volpe and Koenig, P.C.

(57) ABSTRACT

An insufflable prosthesis is provided, that is radiopaque or with a circumferential radiopaque mark, for sutureless and non clamping side-to-side, end-to-end and end-to-side anastomosis, or fast clamping and sutureless wherein vessel graft or any other is inserted or not (whether externally covered or not if using grafts), in the lumen of the prosthesis comprised by an insufflable balloon, whether distensible or not and after being covered by graft, the balloon can be filled with polymerizable fluid, like silicon or cyanoacrylate glue, whether radiopaque or not, by a syringe having unidirectional valve to a needed caliber in order to keep the graft wall jointed and tight in relation to the organ which performs the anastomosis. The insufflable balloon, elastic and distensible, or non elastic and having preset dimensions also comprises non elastic punctiform bars inside that are responsible for keeping constant the distance between the elastic balloon walls.

10 Claims, 3 Drawing Sheets

Inelastic pinpoint lock

Elastic part

INSUFFLABLE PROSTHESIS FOR ANASTOMOSIS

FIELD OF INVENTION

The present invention refers to an insufflable anastomotic device, whether elastic or not, for performing sutureless and without clamping or sutureless and fast clamping anastomosis (if the organ walls are normal) wherein graft vessel, or any other, is inserted inside prosthesis lumen and everted in order to totally cover it and being fixed by any other method or even to it through stitches. After being covered by graft, prosthesis is insufflable with a fluid that may be or not polymerizable, radiopaque or not, or even the prosthesis material being radiopaque or just having a radiopaque circumferential line.

DESCRIPTION OF THE PRIOR ART

A prior art presents several trials provide solutions for anastomotic devices projected to correct vascular abnormalities, which present the following typical features:

The North-American U.S. Pat. No. 3,254,650, of Jun. 7, 1966, describes a method and devices to execute anastomosis procedures by applying with adhesive two separated connectors in a body member and removing this body member portion contained among the connectors, joining the said connection devices for joining the remaining portions of the body member.

The U.S. Pat. No. 3,265,069, of Aug. 9, 1966, describes devices or instruments for use by surgeons in reunion of body ducts, which in the course of operations were separated. The instruments comprise a pair of elongated similar elements and articulatedly connected, in an intermediary manner, and with an support for finger retention in a distal end, comprising a generally cylindrical shape with a cylindrical channel that passes through it in the other distal end, in order to receive tubular body ducts kept by the instrument while the body ducts are reconnected.

U.S. Pat. No. 3,774,615, of Nov. 27, 1973, describes a device to connect the end of interrupted tubular organs without sewing, comprising a connecting ring on which the end of the interrupted organ are pulled, the ring is preferably locked up by a fixation resource. The ring and fixation resource are made of inert material, and preferably a hydrophile gel that can be dilated until its equilibrium or can be a hydrogel incompletely dilated, which is submitted to additional dilatation where it is applied. The connecting ring can be supplied with a groove and can be placed in a ring shaped fixation resource and kept there joining it to the fixation resource in the groove or simply kept by a screw. Two connection rings can also be used and kept joined by a coupling member.

The document U.S. Pat. No. 4,366,819, of Jan. 4, 1983, describes an anastomotic joint for surgery with a graft of coronary artery deviance comprising a mounting of four elements including a cylindrical tube with at least one locking indentation of ring flange in one influx end and a plurality of grooves of locking ring in a flow end; a ring flange with a central opening and a plurality of long and short spigots, the long spigots are engaged in the locking indentation, with a graft engaged among them; a fixation ring with a central opening and a plurality of spigots positioned around the opening; and a locking ring with a opening with a plurality of locking ring edges for engaging with the locking ring grooves. In surgical implants, an aortic wall with a hole engages between the ring flange and the fixation ring and is kept in this position by spigots of the fixation ring, and the four elements engage together forming an integral anastomotic joint. A first alternate modality includes an anastomotic joint of three elements with a combination of fixation ring and locking ring. A second alternate modality includes an anastomotic joint of four elements with a slightly jolted end in a influx end, exposing the graft material in the anastomotic "ostium".

Other prior arts are equally mentioned, base don some information of "The Cardiothoracic Surgery Network". The "Simmetry Aortic Connector System", developed by St. Jude Medical, is a connector made with nitinol, selected by vein diameter with an adventitia removed to allow adjust of the connector and to prevent its displacement by the blood current. Then, the device may make an angle of 90° with the aorta. Among the disadvantages, there is the fact that it can be used only in extreme cases due to the difficult usage of this technique; it did not obtain a satisfactory result in many surgeries and it is being drowned out of market by the manufacturer; it is not applicable in calcified aorta; presents suture; presents contact with blood flow (foreign body); it does not widen the anastomosis area (restrictive anastomosis); performs only one anastomosis at a time; it is a product restrict to end-to-side anastomosis; a great mobilization of the venous graft occurs, damaging it, and can eventually form thrombus; there is a risk of perforation of the posterior wall of aorta; and the adventitia is removed (most resistant vascular layer).

Other known device is the PAS-Port™ System, a device used in 3 steps, and the vein wall is mounted over the device and is manually reversed on it, by tool and adapted to aorta with a angle of 90°. The method alerts that the surgeon shall select with due care the point of aorta and the vein size. The device is made of stainless steel and is available in only one size that allows the use of veins with external diameter of 4 to 6 mm, aorta with an internal diameter of 18 mm. It is available in only one size, limiting its applicability. As disadvantages of this prior art, the device has contact with blood flow (foreign body); it does not widen the anastomosis area (restrictive anastomosis); it uses veins with external diameter of 4 to 6 mm and aorta with an internal diameter of 18 mm; it does not perform multiple nor visceral anastomosis; it performs just only end-to-side anastomosis; a great mobilization of the used biological graft occurs, damaging its inner layer, which generates the formation of thrombus; there is a big risk of kinking at the origin (angle of 90°) and risk of posterior wall perforation in the aorta at the moment the device is introduced under its light; the suture is substituted with disadvantages by stainless steel (9 pins, distant among them, maximizing the risk of bleeding).

Also as prior art, there is the CorLink Device, currently commercialized by Ethicon/Johnson & Johnson, that allows the creation of anastomosis between the ascending aorta and a saphenous vein segment. Aortic Anastomotic Device (AAD) is a self-expanded device with extra luminal nitinol constituted by a de um central cylinder with five interconnected elliptical arches and 2 groups of 5 pins in the end portion of the cylinder. The pins, after the eversion of venous walls in the device, fix the aggregate penetrating into the venous graft wall. A blade makes an opening in the wall of aorta and permits the coupling of AAD, which also fix the wall of aorta by pins. With this device: it poses a serious risk of bleeding, especially in friable aortas, thin, calcified or fibrous, restricting its applicability, also with risks, even in aortas with normal walls; in small gauge anastomosis, there is a risk of thrombosis, hyperplasia, intimal proliferation and fibrosis (reaction to foreign body type in origin of anastomosis) with consequent stenosis resulting in occlusion of anastomosis; sutures are used in some cases; there is cases of infarction caused by equipment; there is a recurring need of re-operations in patients; the device presents contact with blood flow (foreign body); it is not flexible; it does not multiple anastomosis; an inadequate mobilization of venous graft occurs, and can cause damage to its intimal layer, it could form thrombus; it is used only in extreme cases because it is a technique of complex usage; the suture is substituted by stainless steel in contact with blood flow.

Another known device is the St Jude Distal Connector that consists of a stainless steel clip mounted on a catheter, comprising a balloon for subsequent expansion and connector mounting. The catheter is introduced backward from the end, by doing a small hole in the anastomosis site, the clip fixes the vein in the hole, the catheter goes to coronary and releases the connector. The catheter is removed and a suture is done in side-to-side anastomosis. With St Jude Distal Connector, occurrence of leakage problems were detected in 20% of the used connectors; the use of a metallic clip requires due care for handling to avoid distortion in the anastomosis; late angiographies reveal smaller circular diameter of anastomosis made with o St. Jude Distal Connector, when compared to controls made with conventional suture; there is remarkably risk of bleeding and the graft is very mobilized, and lacerations can occur in its inner layer, allowing the formation of thrombus.

The HeartFlo™ is a multi-suture instrument for anastomosis with wires automatically applied in end-to-side and side-to-side anastomosis. The surgeon manually ties the suture wires (10 wires) and concludes the anastomosis similarly to the traditional process. Besides of being a product of complex handling, it makes suture in anastomosis (keeping the undesirable foreign body in the internal origin of the anastomosis) and is restricted to end-to-side and side-to-side anastomosis. There is also an excessive mobilization of graft, and can cause lesions in its intimal layer, which would be the inductor that forms the thrombus.

Another technique and known device is the Solem Graft connector, produced by the Swedish company Jomed. It is constituted by a stent made of nickel and titanium coated with polytetrafluorethylen used to connect the internal thoracic artery the left anterior descending coronary artery. The results has not been satisfactory, because it poses risk of bleeding; there is also an excessive mobilization of graft, probably damaging intimal layers, allowing the formation of thrombus; it is not flexible, by this fact, causes trauma to grafts; it does not make multiple anastomosis, at a single time; presents contact with blood flow (foreign body); and is frequent the need of-operations.

The Magnetic Vascular Positioner System is produced by Ventrica and comprises 4 magnetic rings and the anastomosis is processed by magnetic attraction of 4 ports. However, initial experimental results demonstrate leakage, also a undesired contact of materials with blood flow. On the other hand, it is necessary to be careful to avoid the capitation of excess of tissue among the magnets. With this system, there is also a need of suture in some cases; there is occurrence of infarction caused by equipment; and is frequent the need of-operations in patients; and also requires clamping.

Also, as a device known by the medical area, the Combined Anastomotic Device and Tissue Adhesive, developed by Grundeman & Borst group, combines micro mechanical technique with use of adhesive (glue). The use of this method can result in leakages and need traditional sutures; it is frequent the need of re-operation due to leakage/bleeding; and performs only one anastomosis at a time.

Finally, it is also experimentally practiced anastomosis assisted by laser, where the results are not different from conventional isolated sutures, because there is a need of suture in some cases; there is a risk of bleeding e leakage; and does not perform multiple anastomosis.

Even so divulged nowadays, anastomosis with clamper, by insecurity, and almost totality of surgeons perform conventional sutures throughout the route of anastomosis, with an intention of avoiding leakages and bleedings, it means the use of clampers just makes the procedure more expensive, once the conventional suture is also applied.

In short, the conventional anastomosis, with clamping and with suture, standardized in 1906 by Aléxis Carrel, remains the first choice for any type of anastomosis and organs to be anastomosed.

With an expectation of changing the current situation, the Brazilian patent no. PI 9706197-2, describes and claims a prosthesis for vascular anastomosis, or in any other organ or tissue, without the use of clamping and sutureless, solving, in an elegant and efficient manner, the limitations inherent to prosthesis of the above mentioned prior art, when used in vascular anastomosis performed, mainly in thin aortas, calcified and friable; or in any other application where a clamping of a vein or artery can pose excessive trauma for conditions of a given patient. The prosthesis that is subject of that request allows the embodiment of fast and safe anastomosis, without obstruction of vein or artery lumen of which anastomosis is made, also allows anastomosis in tissues, veins or arteries in bad conditions and never would accept a clamping used in conventional anastomosis. This is achieved by a generally cylindrical shaped prosthesis with a flange orthogonally extending from its external side wall, in a point in the prosthesis length between its ends; the referred flange has openings distributed around its surface. The description of the usage method and specific construction of the prosthesis is presented in the drawings of the descriptive report of that request, as well as the document C19706197-2, Certificate of Addition of the first.

Although these anastomotic devices can be presented as suited to the purposes for which they were projected, they are not so suited for the purposes of the present invention, as described herein below.

SUMMARY OF THE PRESENT INVENTION

The present invention refers to a insufflable prosthetic device, elastic and extendable, having variable dimensions or not elastic having preset dimensions, in biocompatible and resistant material (PTFE, Gor-Tex, etc.) extraluminal, radiopaque, or having a circumferential radiopaque mark, or insufflable with radiopaque fluid, whether polymerizable or not (like cyanoacrylate glue), used for clamping and sutureless side-to-side, end-to-end and end-to-side anastomosis wherein at least one graft vessel or any other is inserted or not in the lumen of the prosthesis (whether externally covered or not if using grafts) and, after being covered by grafts, the prosthesis is insufflated, as a balloon, up to a preset caliber (non elastic prosthesis) and/or desired (elastic and insufflable prosthesis, having dimensions variable to insufflation), in order to maintain graft wall united and tight in relation to organ wall in which anastomosis is performed. The graft is reverted by jacketing to cover insufflable prosthesis that, when insufflated, eliminates contact of strange bodies to anastomosis interior. Prosthesis may also have a variety of dimensions and formats to simultaneously accommodate several sizes and types of grafts.

An objective of the present invention is to proportionate an insufflable and elastic anastomotic device, balloon-like, enabling to regulate its caliber exactly to organ incision diameter and to graft caliber.

Another objective of the present invention is to proportionate an insufflable anastomotic device having preset measures what enables making it without clamping and sutureless, wide, of one or several grafts in a simultaneous way.

Another objective of the present invention is to proportionate an anastomotic device for any type of anastomosis (side-to-side, end-to-end and end-to-side) sutureless and without clamping between any tubular organ.

Another objective of the present invention is to proportionate an anastomotic device that does not insert any other strange bodies inside anastomosis grafts.

Additional objectives of the present invention and other modalities will appear as depiction proceeds. Such modalities will be depicted in enough details enabling those skilled in the art to implement the invention. Besides, it is to be understood that other modalities may be used and that structural changes may be performed without withdrawing from the scope of the invention. In the attached drawings, characters of similar reference designate the same parts or similar throughout several views.

The following detailed description is not to be taken as limiting and the scope of the present invention is better defined by attached claims.

BRIEF DESCRIPTION OF THE DRAWINGS

So that the invention may be better understood, it will now be described by means of example, referring to attached drawings, which.

DESCRIPTION OF PREFERRED MODALITIES

Figure 1:
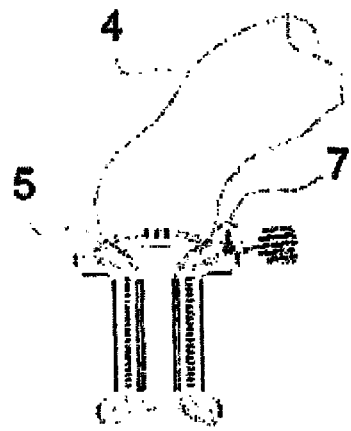
FIG. 1 illustrates insufflable prosthesis before its insufflation with a syringe having radiopaque fluid; with unidirectional valve or a tap and the prosthesis already totally covered by graft everted end, exceeding its external flange.

Referring now to the drawings in which characters of similar reference denote similar elements for all several views, the figures illustrate one of the embodiments of the present invention in a prosthesis format for insufflable anastomosis.

Figure 2:
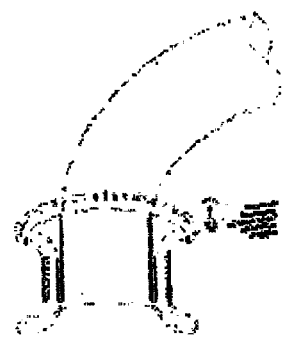
FIG. 2 illustrates prosthesis covered by graft being insufflated.

FIGS. 1 and 2 illustrate insufflable prosthesis that is nonelastic and non-expansible having preset dimensions after insufflated. Such prosthesis has bobbin format, having internal and external flanges and grooves in its external surface to anchor its grafts. Its flange may have small circumferential handles in its external edge or inferior face wherein the graft or anastomotic trunk (formed by joining distal ends of multiple grafts, in desired extension and caliber) may be fixed with simple stitches so that it does not slide during insufflation.

Prosthesis material must be resistant, biocompatible, radiopaque or having only a radiopaque circumferential line, or even being insufflated with radiopaque fluid. Radiopaque prosthesis by any means makes facilitates, diminishes expenses and risks for patients and time for contrasted restudies. Only with simple radioscopy we can identify anastomosis local, wherein catheters are correctly directed for light, with no need of contrasts, that most of time are toxic and expensive (neurotoxic etc.). Here also a catheter is enough for catheterization instead of several as it is usual in homodynamic restudies procedures, for example. The cost will significantly decrease. Imagine the benefits for patients having conterminal renal function that will be induced to renal failure and will need hemodialysis if they used great amounts of neurotoxic contrasts in this restudy. With a simple chest RX it is possible to learn how many grafts were used, obviously if the anastomotic trunks there have been placed radiopaques marks like titanium clip externally to the grafts after being individualized outside the prosthesis. The following technique may be employed in order to perform a sutureless and non clamping end-to-side anastomosis: graft or anastomotic trunk is passed through the light of insufflable prosthesis totally covering it up to few millimeters above its superior flange. The trunk may be fixed to itself by stitches or to the circumferential handles existent on the external edge. A suture in a bag is done in a small area of the organ wall, an incision in the center and a temporary tampon with two clamps or digitally. The prosthesis is discretely insufflated to assume a bobbin format and to become more resistant; the anastomotic set is inserted in the incision; the suture in bag is smoothly tight. The complement of prosthesis insufflation may be with polymerizable fluid like cyanoacrylate glue in which in little time guarantees maintenance of anastomosis form even though for any improbable reason the balloon 5 is damaged. The tap is closed and the empty syringe is withdrawn. The bag suture tiding is smoothly completed, external, serous or serous muscled or totally in organs with sick walls.

Figure 3:
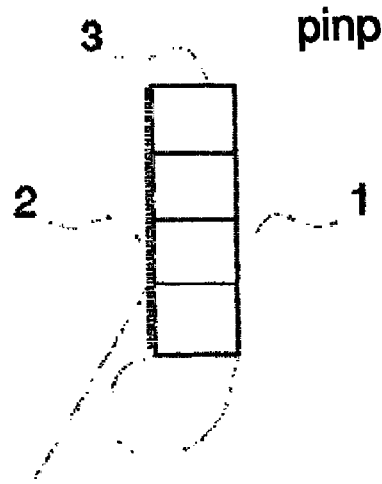
FIG. 3 illustrates elastic and insufflable prosthesis, having variable dimensions, non elastic punctiform bars between internal and external layers of the balloon, responsible for keeping constant the distance between the layers.
Figure 4:
FIG. 4 illustrates a cut view that separates internal and external layers from insufflable prosthesis in a way of illustrating fixation local of non elastic punctiform bars.
Figure 5:
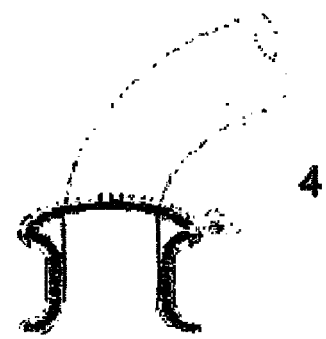
FIG. 5 illustrates insufflable prosthesis at the end of anastomosis having radiopaque fluid inside of it.

FIGS. 3, 4 and 5 represent a prosthesis which internal 1 and external 2 layers are elastic and extensible by insufflation allowing, like a birthday balloon, their internal measures to increase or decrease in order to accommodate grafts of variable calibers. In order to not occur an extension of internal layer 1 inlet occluding its light, non elastic punctiform bars 3 will join to external layer 2, as illustrated on FIGS. 3 and 4. External layer preferably will be more resistant to insufflation than internal layer. Thus, by expanding it will bring together the internal layer due to non elastic bars 3 that join them. Even though the layers have the same tensile strength, they expand in the same direction and simultaneously due to non elastic bars that join them, always increasing internal diameter in higher pressures and volume of injected fluid. Obviously there will be a superior limit for its expansions before they break up. Thus, with this prosthesis, grafts 4 from several calibers can be used the same way without having any difficulty in evert them in order to externally cover it or its heads. Also, and likewise the one described, an anastomosis wide, multiple, in a single time, sutureless and with out clamping and between any kind of two or more tubular organs may be done.

Figures from 1 to 5 may also represent an insufflable prosthesis 12, low profile and high caliber, that may be used for any kind of anastomosis whether covered by grafts or not. In a sutureless and without clamping end side anastomosis, for instance, grafts 4 or trunk may no pass through its light but cover its external flange. In this case, after externally and totally cover it with grafts or trunk, the prosthesis is insufflated and they are fixed on it by any method like suture, glue elastic circular stitch (that follow prosthesis insufflation) etc. The prosthesis is partially deflated, the organ wall in the center of the suture bag is incised, and it is partially inserted in the light of the organ. The suture in bag is smoothly tight, its insufflation is completed, and the suture in bag tiding is finished. The tap is closed and the syringe is withdrawn. Thus the fluid, like blood, will be in touch with the prosthesis tissue. In order to minimize risk of reactions like strange body and thrombogenicity in the site of anastomosis, these prosthesis may be covered by endothelial lyophilized adhered homologous tissue, may be with biological glue, a microporous that exists in its internal surface for this purpose.

Figure 6:
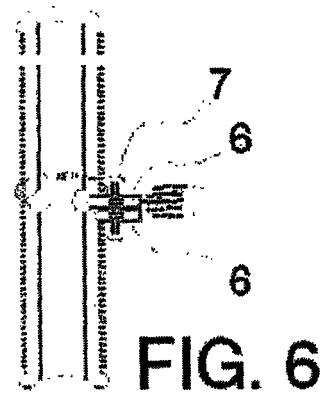
FIG. 6 illustrates insufflable prosthesis that contains internal insufflable occlusion balloon that is not insufflated, at half distance from the flanges.
Figure 7:
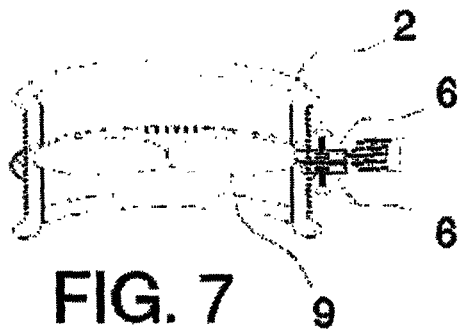
FIG. 7 illustrates occlusion balloon insufflated occluding prosthesis lumen.
Figure 8:
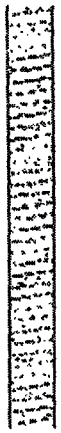
FIG. 8 illustrates a sutureless and non clamping side-to-side anastomosis, in which occlusion balloon is still insufflated, occluding light from prosthesis.
Figure 8:
Figure 9:
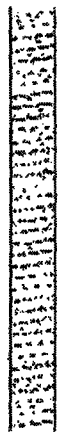
FIG. 9 illustrates the end of sutureless and non clamping side-to-side anastomosis with occlusion balloon no more insufflated and light of prosthesis being permeable.
Figure 9:
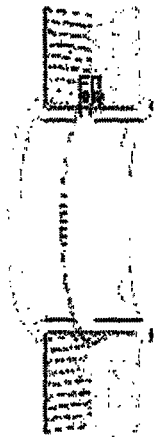

FIGS. 6, 7, 8 and 9 represent an insufflable prosthesis, elastic and extensible, or non elastic and non extensible, having double flange which perfusor 6 for insufflation is located at half distance from flanges in its external surface 2. Internally, tubular member has, as seen in FIGS. 6-8, an insufflable balloon of occlusion 9, elastic and distensible, exactly located half the tubular member, which perfusor 6 exteriorizes, contiguously or in opposite local to prosthesis perfusor which, when insufflated totally occludes the light of prosthesis (intraluminal "clamping" by balloon). Perfusores 6 have unidirectional valves or taps 7. Tubular member may have grooves in its external surface and circumferential handles at the same level of outlets of taps or valves in order to fix with simple stitches the graft or anastomotic trunk that covers it (anastomotic trunk is the joint of the end of several grafts or its total extension, that is, for example a graft of 20 cm length and 3 mm diameter if transversely sectioned in half, in two equals halves and longitudinally opened in all its extension and sutured or jointed between them by any safe method, it will form an anastomotic trunk having 10 cm length and approximately 6 mm diameter).

With this prosthesis it is very easy to perform sutureless and without clamping side-to-side anastomosis or any other modality of anastomosis. Sutureless and without clamping side-to-side anastomosis could be performed as represented in FIGS. 6-9: the prosthesis is insufflated and the internal balloon occludes its light. The suture in bag in the side walls of the organs to be anastomosed is performed. An incision in the wall of the center of the suture in bag is done. One of the flanges is inserted; the suture in bag is smoothly tide around tubular member. An incision in another organ wall also in the center of the suture in bag is done, digitally tampon it, another flange is introduced, the suture in bag is smoothly tide also around tubular member. The prosthesis insufflation finishes. The occlusion balloon is deflated allowing blood flow or of any other fluid. An end-to-end anastomosis is easier to be performed following the same technique described for the side-to-side one, only substituting sides by proximal and distal organ stubs, side entering with flanges. After total insufflation of prosthesis, the suture in side bag is tide where the flanges enter, the occlusion balloon is deflated opening the light of the prosthesis and the organ wall is circumferentially tide around its tubular member, making the flow to be totally directed to the prosthesis light.

Figure 10:
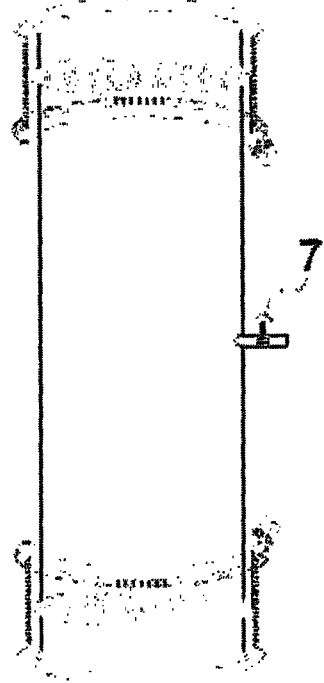
FIG. 10 illustrates a long prosthesis, having in each end an insufflable balloon in a bobbin format, jointed by a non elastic tubular member whether folded or not which has at half distance from the ends or any local a tap for fluid inlet or outlet (for example air aspiration).

FIG. 10, represents a prosthesis having double flange, insufflable, separated by a long tubular and non insufflable member. This tubular member, folded or not, may have or not an internal occluding balloon since it may be conventionally externally. Occluding balloons may be internally sited in each one of its ends in a bobbin format, as showed in FIG. 10. Also its non elastic long tubular member may have a tap 7 in its half for inlet and outlet of fluids (example, for air withdrawing) also represented in FIG. 10. This long prosthesis allows anastomosis in distant stubs of any organs making sutureless and non clamping side-to-side, end-to-end and end-to-side anastomosis. These anastomosis may be done in different organs, for example, ureter to bladder; coledoco to duodenum, jejunoum or ileus; right ventricle to pulmonary artery; central or periphery pulmonary systemic shunt; correction of aneurysms outside the sick area by isolating it after anastomosis performed; anastomosis of tube in uterus, etc. Of course that, preferentially, this prosthesis should be internally covered with biologic autologic or homologous treated tissues, or even endothelial lyophilized tissue, as already described. The technique for its usage is similar to the ones already described.

Figure 11:
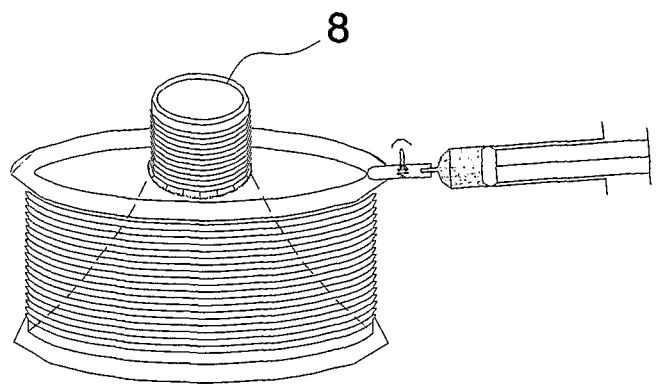
FIG. 11 illustrates an insufflable prosthesis, low profile and thick caliber in the intraluminal part, having a mobile, folded, insufflable head, having internal conical tubular member.
Figure 12:
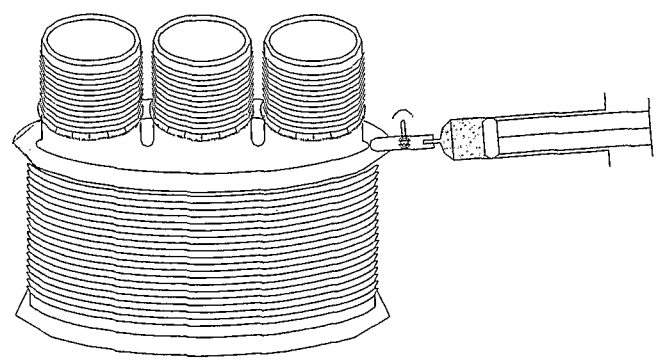
FIG. 12 illustrates an insufflable prosthesis, low profile and thick caliber in the intraluminal part, having a mobile, folded, insufflable triple head, having internal conical tubular member.

FIGS. 11 and 12 represent insufflated prosthesis with caliber intraluminal part and heads 8 in a variable number also insufflable which sum of internal diameters of the heads is equals to internal diameter of intraluminal part. Also that, internally, prosthesis is conical directed for each head in order to guarantee laminar flow generation in its inside. Its heads 8 have in its base handles that enable to fix with simple stitches the grafts that cover them or also to be fixed to them by any type of glue and circular joint.

Similarly to technical description right above, the anastomotic set is applied in the center of a suture in bag on the organ wall, sutureless and without clamping performing the wide, multiple, in a single time, having one single prosthesis anastomosis, in which blood or any other fluid can be in touch with the material of the prosthesis. In this case, as hereinabove described the prosthesis could be internally covered by endothelial homologous lyophilized tissue, fixed by any method, for example biological glue, partial microporous (or internally rugged surface) that existed in its internal surface. Thus, it implies that it must be understood that insufflable prosthesis for anastomosis and its components above described are only some of the modalities and examples of situations that might occur the real scope of the object of invention that are defined in the claims.

The invention claimed is:

1. Prosthesis for anastomosis comprising at least one flange, at least one tubular body having an external surface with grooves, and an internal inflatable occlusion balloon, which, when inflated, temporarily occludes a lumen, wherein the at least one tubular body is an inflatable balloon, comprising a distensible elastic part.

2. Prosthesis, according to claim 1, wherein the elastic part comprises an internal layer; an external layer and non elastic punctate members disposed between the layers.

3. Prosthesis, according to claim 1, wherein the prosthesis is comprised of a radiopaque material.

4. Prosthesis, according to claim 1, further comprising at least one circumferential radiopaque line in the at least one flange.

5. Prosthesis, according to claim 1, wherein the balloon is inflated by a syringe comprising a unidirectional valve.

6. Prosthesis, according to claim 5, wherein the balloon can be inflated with radiopaque fluid.

7. Prosthesis, according to claim 6, wherein the fluid is polymerizable.

8. Prosthesis, according to claim 1, wherein the elastic part comprises an internal layer; an external layer and non elastic bars are disposed in uniform spaces maintaining a constant distance between the internal layer and the external layer of the elastic part.

9. Prosthesis, according to claim 1, further comprising at least one inflatable head external to the prosthesis.

10. Prosthesis, according to claim 9, wherein the head also has a conical trunk.

* * * * *